(12) United States Patent
Maeda et al.

(10) Patent No.: US 7,682,630 B2
(45) Date of Patent: Mar. 23, 2010

(54) ANTITUMOR AGENT AND PROCESS FOR PRODUCING THE SAME

(75) Inventors: Hiroshi Maeda, 21-24, Koto 3-chome, Kumamoto-shi, Kumamoto 862-0909 (JP); Khaled Greish, Kumamoto (JP)

(73) Assignee: Hiroshi Maeda, Kumamoto (JP)

( * ) Notice: Subject to any disclaimer, the term of this patent is extended or adjusted under 35 U.S.C. 154(b) by 0 days.

(21) Appl. No.: 10/514,892

(22) PCT Filed: Feb. 2, 2004

(86) PCT No.: PCT/JP2004/000993

§ 371 (c)(1), (2), (4) Date: Nov. 17, 2004

(87) PCT Pub. No.: WO2004/103409

PCT Pub. Date: Dec. 2, 2004

(65) Prior Publication Data

US 2005/0208136 A1 Sep. 22, 2005

(30) Foreign Application Priority Data

May 26, 2003 (JP) ............................. 2003-147852

(51) Int. Cl.
*A61K 47/48* (2006.01)
*A61K 33/24* (2006.01)
*A61K 9/51* (2006.01)

(52) U.S. Cl. .................... 424/486; 424/649; 514/34

(58) Field of Classification Search ............... 424/78.27
See application file for complete search history.

(56) References Cited

U.S. PATENT DOCUMENTS

| 4,762,885 A | | 8/1988 | Maeda et al. | |
|---|---|---|---|---|
| 5,527,805 A | * | 6/1996 | Smith et al. | ................. 514/280 |
| 6,080,877 A | * | 6/2000 | Swindell et al. | ............. 549/510 |

FOREIGN PATENT DOCUMENTS

| EP | 260796 A1 * | 3/1988 |
|---|---|---|
| EP | 0 087 957 | 11/1988 |
| JP | 58-149903 | 9/1983 |
| WO | 01/52893 | 7/2001 |
| WO | 02/45689 | 6/2002 |

OTHER PUBLICATIONS

Yasuhiro Matsumura et al. Reduction of the Side Effects of an Antitumor Agent, KRN5500, by Incorporation of the Drug into Polymeric Micelles, Jpn. J. Cancer Res. 90, 122-128, Jan. 1999.*
Hiroshi Maeda et al. Mechanism of tumor-targeted delivery of macromolecular drugs, including the EPR effect in solid tumor and clinical overview of the prototype polymeric drug SMANCS, Journal of Controlled Release vol. 74, Issues 1-3, Jul. 6, 2001, pp. 47-61.*

Tetsuya Hamaguchi, et al., Molecular Cancer Therapeutics, 2001, vol. 2 No. 3, pp. 328-336.*
Tatsuro Ouchi and Yuichi Ohya, Macromolecular Prodrugs, Prog. Polym. Sci., vol. 20, 211-257, 1995 Elsevier Science Ltd.*
Hiroshi Maeda, SMANCS and polymer-conjugated macromolecular drugs: advantages in cancer chemotherapy, vol. 46, Issues 1-3, Mar. 1, 2001, pp. 169-185.*
Supplementary European Search Report issued Nov. 12, 2008 in counterpart European Application No. 04 70 7295.
Wang et al., "Synthesis and Characterization of Polymer Derivatives of cis-Platinum Complexes", Chinese Journal of Polymer Science, No. 4, (1987), pp. 359-369.
Kalčić et al., "Macromolecular prodrugs, VII. Polymer-dopamine conjugates", International Journal of Pharmaceutics, vol. 136, (1996), pp. 31-36.
Patel et al., "Polymeric prodrug: Synthesis, release study and antimicrobial property of poly(styrene-*co*-maleic anhydride)-bound acriflavine", Die Angewandie Makromolekulare Chemie, vol. 263, (1998), pp. 25-30.
International Search Report mailed Apr. 27, 2004 in International (PCT) Application No.PCT/JP2004/000993, Abstract.
Khaled Greish et al., "Shingata Micelle-zai SMA-Pirarubicin; Chomci na Koshuyo Sayo to Teidokusei", Drug Delivery System, vol. 18, No. 3, 2003, p. 254 I-C-22.
Tetsuya Hamaguchi et al., "DDS no Rinsho Donyu", Molecular Cancer Therapeutics, (2001), vol. 2, No. 3, pp. 59-68, No Translation.
Kazunori Kataoka, "Seiganzai Niho Kobunshi Micelle ni yoru Gan no Hyoteki Chiryo", Molecular Cancer Therapeutics, 2001, vol. 2, No. 3, pp. 4-10, No Translation.
Yasuhiro Matsumura, "DDS Seizai no Kaihatsu to Rinsho Koka", Antibiotics & Chemotherapy, vol. 19, S-1, 2003, pp. 64-71, No Translation.

* cited by examiner

*Primary Examiner*—Michael G Hartley
*Assistant Examiner*—Nabila G Ebrahim
(74) *Attorney, Agent, or Firm*—Wenderoth, Lind & Ponack, L.L.P.

(57) ABSTRACT

The present invention relates to polymeric antitumor agent which is formed in polymeric micelle complex by intermolecular bonding or mutual interaction between styrene maleic acid copolymer (SMA) and low molecule antitumor agent which is anthracyclins drug such as pirarubicin, doxorubicm, epirbicin, daunorbicin, acralbicin, or alkaloid antitumor agent such as cis-platinum, and taxol These polymeric antitumor agents may improve specificity to cancer cells so that it improves antitumor effect, while it may not be concentrated at normal organ or tissue, so that adverse effect may be diminished. These polymeric antitumor agents may be prepared by dissolving SMA and low molecule antitumor agent in aqueous solution, then in the presence of aqueous soluble carbodiimide, amino acids, or polyamine, adjusting pH to form micelle complex and recovering polymer fraction.

4 Claims, 7 Drawing Sheets

ANTITUMOR AGENT AND PROCESS FOR PRODUCING THE SAME

This application is a U.S. national stage of International Application No. PCT/JP2004/000993 filed Feb. 2, 2004.

FIELD OF THE INVENTION

The present invention relates to a group of polymeric antitumor agents, forming high molecular weight micelles complex, having selective tumor targeting capacity and long term retention in tumor, thereby exhibiting highly effective cancer treatment with greatly reduced side effects to the normal organs and tissues.

More precisely, the present invention relates to high molecular weight polymeric antitumor agents, forming high molecular weight micelles complex by molecular binding or interaction of low molecular weight antitumor agents, such as anthracyclin or platinum derivative with styrene-maleic acid copolymer (hereinafter referred to SMA).

The present invention also relates to the method of manufacturing the same.

BACKGROUND TECHNOLOGY

Since the discovery of doxorubicin(adriamycin . . . Formula (1)) in 1969 by Di Marco and his coworker (Cancer Chemotherapy Reports, Part 1, 53, 33-41, 1969), the class of anthracyclin antitumor agents expanded greatly. In 1979 pirarubicin (THP-adriamycin . . . Formula (2)) was discovered by Umezawa et al during a search of new anthracyclin antibiotics. Among the 4'-O-substituted compounds, THP-adryamicin has less toxicity than other anthracyclin antitumor agents (Gan To Kagaku Ryoho, 15, 2819-27, 1988).

Anthracyclins antibiotics are known for its potent cytotoxic effect that is known to involve multiple mechanisms of cell killing. Generation of the oxygen radical by quinone group in its molecule promotes its DNA intercalating property and topoisomerase inhibitory mechanisms. All these effects lead to potent cancer cell killing. Pirarubicin, being relatively a new member of this group, has its unique DNA and RNA synthesis inhibitory action, more active than doxorubicin, with reduced cardiotoxicity.

Unfortunately the cytotoxic effect of these low molecular weight antitumor agents, such as anthracyclin or cis platinum, like many others, lack specificity to cancer cells that leads to sever side effects particularly towards rapidly dividing cells such as bone marrow cells and cells of the gastrointestinal tract. Furthermore, they affect slowly dividing or more stable tissues such as cardiac and hepatic tissues chronically. These side effects are the main factors limiting dose escalation of such powerful drugs.

To eliminate such side effects of these antitumor agents, the tissue distribution of drug plays a crucial role. We found that the molecular weight of the drugs are key to the question, namely drugs of low molecular weight drugs, for example, molecular size less than 10 KDa, are readily distributed in various normal organs tissues or tumor tissues indiscriminately through simple diffusion, and they are eventually eliminated into the bile by the liver and/or into urine through renal excretion. In case of doxorubicin and pirarubicin with molecular weight of 543.5 and 627.6, respectively, their distribution in the normal organs, i.e. the cardiac or bone marrow tissues, limit the effective use at high dose of these low molecular weight drugs for complete tumor eradication.

Problems to be Solved

This situation of toxicity and efficacy becomes great contrast between high molecular weight drugs vs. low molecular weight drugs. Namely macromolecular drugs of size above 40 KDa, where such drugs accumulate and remain more in tumor tissue for a long time due to the unique phenomenon of tumor tissue, which we discovered sometime ago: i.e. enhanced permeability and retention (EPR) effect of macromolecular or lipid drugs in solid tumors (Cancer Res., 44, 2115-2121, 1984; ibid, 46, 6387-92, 1986; Anticancer Res., 13, 1287-1292, 1993).

EPR phenomenon is attributed to anatomical and pathophysiological alternations in tumor tissues, such as increased vascular density by angiogenesis, lack of smooth muscle layer in solid tumor vessels and impaired lymphatic recovery. Pathophysiological changes in solid tumor are brought about by extensive production of vascular mediators such as bradykinin, nitric oxide, prostaglandins, matrix metalloprotinases (MMPs), VEGF/VPF and others resulting in enhancement of EPR effect that are not seen in normal tissues (e.g. Cancer Res., 58, 159-165, 1995; J. Control. Release, 74, 47-61, 2001; Advan. Enzyme Regul., 41, 189-207, 2001)

Previously, we had developed the first polymeric drug SMA [poly(styrene-co-maleic anhydride half n-butyrate)] conjugate with covalently linked to the proteinaceous antitumor agent, neocarzinostatin (NCS), which is named SMANCS (Japanese Patent (JP) No.1,549,302, JP 1,545,131, JP 2,556,865 and U.S. Pat. No. 2,556,865). This was the first antitumor polymeric drug in the world.

SMA confers unique pharmacological characters when compared with the parent low molecular weight drugs. Namely, SMA conjugates would become capable of rapid non-covalent bond to albumin, and hence that confers tumor tropism by EPR effect by virtue of increase of the molecular weight, thereby has excellent tumor targeting capacity.

Secondly, it has immunopotentiation (Oda T. et al., Proc. Soc. Exp Biol. Med., 181, 9-17, 1986; Masuda E and H Maeda, Cancer Res., 56, 1868-1873, 1996).

DISCLOSURE OF THE INVENTION

The inventors of present invention aimed at a method for improving selective solid tumor targeting capacity of antitumor agents such as anthracyclins which affect normal cells adversely, accordingly reduce the side effects. When SMA polymer was attempted to attach to antitumor agents, unique polymeric antitumor agent was obtained; these drugs formed micelle complex so that it behaves as a polymer and indicates EPR effect more extensively, resulting in improved antitumor effect and lesser side effects, and also better stability at room temperature, in contrast to SMANCS which is prepared by polymerization based on mere covalent bond of SMA and NCS.

Drugs other than anthracyclin, such as cis-platinum, forms polymeric micelle complex by combining with SMA, thus obtained polymeric antitumor agents also have selective solid tumor targeting capacity Briefly, the present invention relates to polymeric antitumor agent, which forms polymeric micelle complex by combining low molecular weight antitumor agent with SMA.

More preferably the present invention relates to polymeric antitumor agent, which forms polymeric micelle complex by combining SMA and anthracyclins antitumor agents, such as pirarubicin, doxorubicin, or cis-platinum.

MOST PREFERABLE EMBODIMENT FOR CARRYING OUT THE INVENTION

Figure 1:
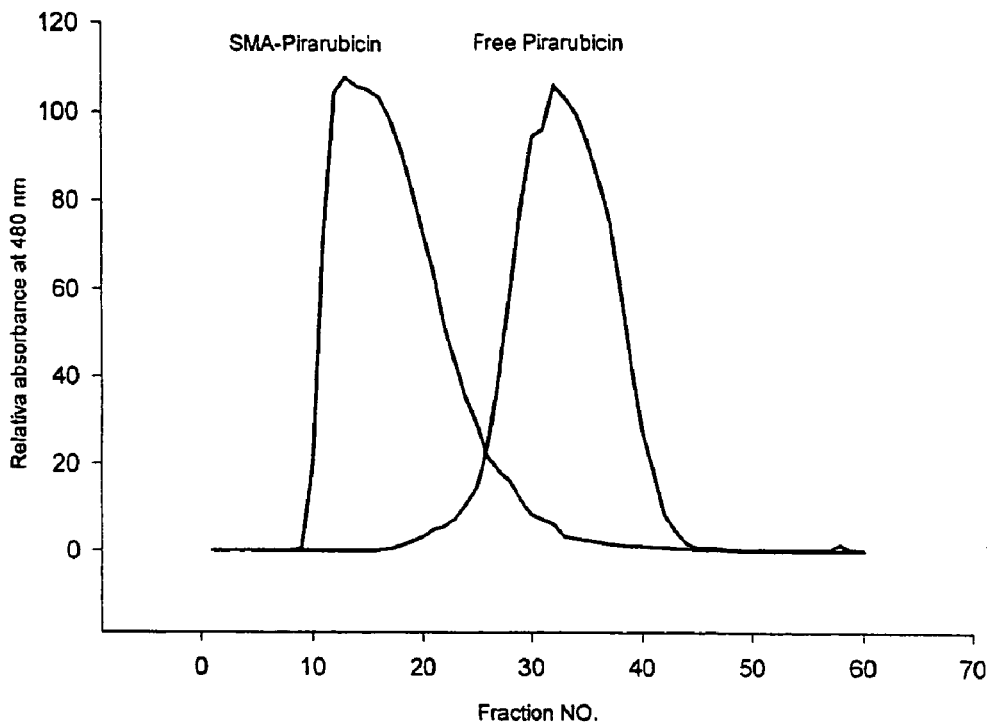
FIG. 1 is gel chromatogram indicating the increase of molecular size of pirarubicin after its bonding with SMA.

While the low molecular weight antitumor agent used in the present invention is not restricted if only they form polymeric micelle complex with SMA, anthracyclins antitumor agents are preferred. Anthracyclins antitumor are antibiotics having glycoside structure of 7,8,9,10-tetrahydro-5,12-naphthasenquinone of which structure are illustrated in Formula (1) and (2).

Example of Anthracyclins may be pirarubicin, doxorubicin, epirbicin, daunorubicin or acrarbicin. Among them, doxorubicin (Formula (1)) and pirarubicin (Formula (2)), are more preferred.

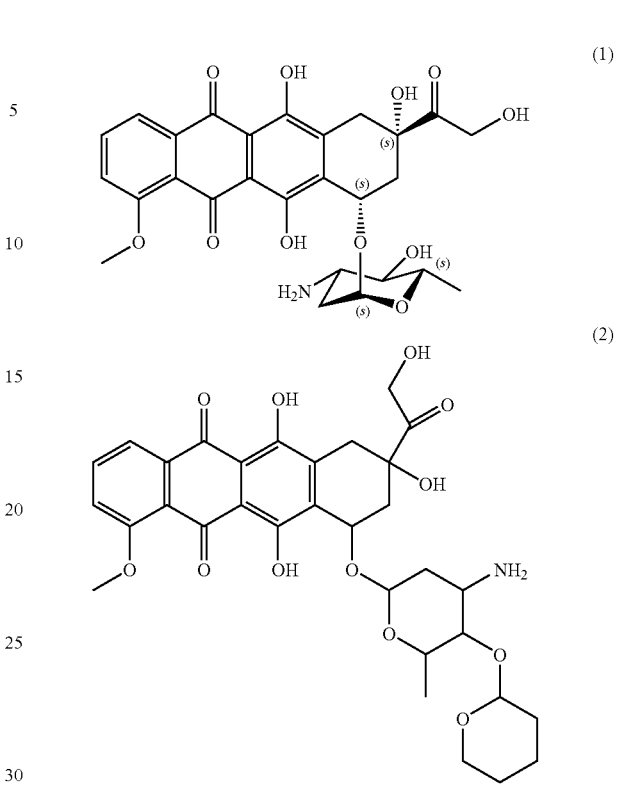

Cis diamine dichloro platinum illustrated by Formula (3), are antitumor agent called as cis-platinum. Such a heavy metal chelate, as well as alkaloids such as canptotecin, taxol and the like can also form SMA micelle complex to be polymeric antitumor agents.

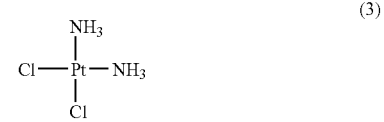

SMA which is the polymerizing agent in the present invention is obtained by copolymerization of styrene with maleic acid. Since SMA is copolymer having styrene and maleic acid as indispensable ingredient, it has basically monomer unit of styrene shown by the formula (4), but monomer unit of maleic acid may be partially half alkyl or acyl esters or maleic anhydride as shown by the formula (5)(Maeda H. et al., J. Med. Chem, 28, 455-61, 1980).

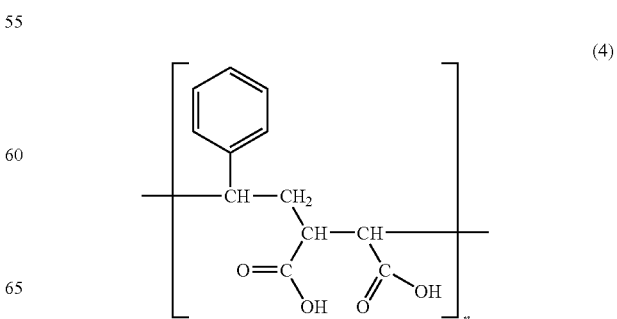

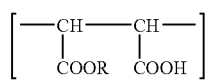

(R in the formula (5) is alkyl or acyl residue of carbon 1~4. In the present invention, half alkyl esterized styrene-maleic acid copolymer, of which a part of R is butyl residue, may be favorably used.

While SMA can have various molecular weight range, most preferable size of SMA used as polymerizing agent in the present invention is from trimmer (about 660 Da) to above 40 KDa While many doxorubicin complexes or conjugates had been developed, the use of SMA as the new polymeric carrier or micelle former is not reported. As exemplified by SMANCS, SMA would be advantageous over existing polymers, because of following reasons.
(1) Half decay term in plasma concentration can be greatly extended by anionized by polyanion.
(2) The complex gets lipophylic due to lipophylicity of styrene so that oleaginous/perolal drugs may be prepared.
(3) It can be hydrophilic drugs as well as lipophilic drugs
(4) It may bond to albumin so that it behaves as polymer of molecular weight of a few ten kilo to a few hundred kilo Daltons so that the EPR effect further increases.
(5) It is amphophylic so that it has high micellizeability
(6) It has capability of immune activation
(7) This micelle complex has great loading capability of drug
(8) It can be produced through simple process
(9) It may improve the stability SMA, also have multiple functional carboxylic group (e.g. ~14 groups per chain of 7 repeating units), which can be utilized to react to cross-link with amino or hydroxyl group of multiple compounds. Another added advantage of the invented SMA-anthracyclin polymeric drugs is related to its acquired lympho-tropic characteristics that become advantageous against lymphatic metastasis. Namely, high distribution in the lymphatics was observed (H. Maeda et al, Gann, 73, 278-284, 1982).

This copolymer of styrene and maleic acid has favorable biological properties such as capacity to rapidly make non-covalent bond to albumin (Kobayashi et al., J. Bioactiv. Compat. Polymer, 3, 319-333, 1988), tumor tropism (Maeda H., Matsumura Y, Cancer Res., 46, 6387-6392, 1986), and immunopotentiation (Oda T. et al., Proc. Soc. Ex. Biol. Med., 181, 9-17, 1986).

In addition to its physicochemical properties as being amphiphilic nature, SMA facilitated highly enhanced the cellular uptake due to existence of styrene and maleic acid (Oda T. et al, J. Nat. Cancer Inst., 79, 1205-1211, 1987).

In the reaction of SMA with low molecular weight drugs, various derivatives of SMA, such as maleyl bicarboxy form as well as anhydrous form, or half alkyl or acyl esters of maleic anhydride. The reaction may be also carried out after hydrolysis or alcoholysis.

Preparation method of high molecular weight micelles complex by the reaction of SMA with low molecular drugs is explained taking the case of anthracyclin antitumor agent.

SMA hydrolyzed in alkaline aqueous solution and antitumor agent are dissolved in aqueous solution, water soluble carbodiimide is added to the mixture, allowing to react at pH of 7 or lower, preferably at pH of 2-5, under stirring. By the subtraction reaction between amino group of anthracyclin and carboxyl radical of SMA, amide bond, ester bond, or non-covalent bond, such as ionic bond or hydrogen bond is achieved.

Non-covalent bond, such as ionic bond or hydrogen bond can be also achieved by the reaction in the presence of amino acids or polyamine to the mixture at pH7 or lower pH, preferably at pH of 2-5, under stirring.

L-arginine, L-ornitine, or lysine are used as amino acid, among them L-arginine is most preferable. Spamine and spamidine are most preferable among the polyamine.

Then pH is raised to over 8 preferably 10-12 to deprotonate free amino groups. Finally pH is adjusted to 6-8 using 0.1 M HCl. Recovering of polymer by ulterafiltration and/or column chromatography is followed. During these procedure SMA micelles entrapping low molecular weight drugs, accompanying conformational changes and molecular interaction will proceed, thus producing micelle form.

As described previously, polymeric antitumor agent in the present invention does not require any additives, such as surfactants for micellization. In the presence of polyamine, antitumor agent and SMA alone are used for stable micelle formation of SMA-antitumor agent micelle complex. Dehydration condensation reaction process is not needed to form micelle complex. This is one of the advantages of the present invention.

Polymeric micelle complex in the present invention may be formed by the reaction of low molecular weight drug and SMA (hydrolyzed), so that the drug is trapped in the micelle. In some cases, the drug is bonded through either cross-link by covalent bond with SMA, ionic bond or non-ionic bond directly. However it is not necessary to be bound chemically (covalent binding in amide structure).

SMA micelle complex thus obtained has unique pharmacological properties compared with parent low molecular weight antitumor agents. Firstly, it has selective delivering ability to the tumor tissues and long term releasing ability verified by the EPR effect, therefore, high therapeutic concentration in tumor tissues with high durability is attained. Moreover, it secures the physiological functions of normal critical organs and tissues, such as cardiac tissue, the bone marrow, or the kidney.

It dose not exist in parent low molecular weight antitumor agents. The higher safety in animal models as described herein was also confirmed.

The SMA-micelle complex according to the present invention has the capacity to bind with plasma proteins, such as albumin, fibrin or lipoprotein, predominantly, it rapidly forms non-covalent bond with albumin. Upon iv injection (intravenous injection) of the drug of the present invention, retention time in circulated blood is remarkably prolonged.

Addition of hydrophobic nature gives wide range of formulation possibilities, e.g. aquas formulation for iv, and oily formulation, especially lipiodole formation for intra arterial or oral delivery, and other various administration method may be applied. Negative charge would enable prolonged in vivo half-life in contrast to positively charged polymers that usually have very short in vivo half-life.

Apparent molecular weight of the micelle complex in the present invention may be greater than 10 Kda, preferably greater than 50 Kda for the purpose of the invention. The apparent molecular weight is defined as a milecular weight of substance associated in an aqueous solution through inter molecule mutual affinity, determined by molecule sieve method, ultra filtration method, ultracentrifugation method or light scattering method in the solution.

Upon the reaction of both constituents, i.e. SMA and either pirarubicin or doxorubicin, they are expected to undergo cross-linking reaction and conformational changes resulting in an apparent molecular weight >10 KDa. Further increase in apparent molecular weight can be observed after iv injection due to non-covalent bond to albumin. Increase in apparent molecular size will result in wider area under the plasma concentration curve (AUC). This means prolonged duration of action without elimination and leads to the observed EPR-effect, high drug accumulation in the tumor tissues, i.e. several folds of plasma level and much more than normal tissue as well as prolonged period of drug action. Consequently, this results in augmentation of the antitumor effect while much reduced systemic side effects.

EXAMPLES

Example 1

Preparation of SMA pirarubicin micelle complex (1) 10 mg/ml of SMA was dissolved in 10 ml water and pH was adjusted to 12 and heating at 5° C. for 4 hours to obtain hydrolyzed SMA.

(2) Pirarubicin at final concentration of 10 mg/ml in $H_2O$ (10 ml) was added and mixed by stirring with a magnetic bar in a 100 ml beaker at room temperature.

(3) pH of the mixture readjusted to 5 under stirring with drop-wise addition of 0.01 M HCl. Ethyl-dimethyl aminopropyl carbodiimid (EDAC), (Sigma Chemical, St. Louis, Mo., USA), was then added at 10 mg/ml (10 ml total/final volume) in 10 aliquots, each addition with 2 minutes intervals and allowed to react for 30 minutes. Colored precipitates will be formed which can be collected by centrifugation or filtration. The yield based on pirarubicin is 99%.

(4) Precipitates were washed with cold acidic water (pH lower than 5.0) 2 times, and then dissolved in $H_2O$ by adjusting pH to 10, then bring down to pH 7. Dialysis with visking tube and ultra filtration with 10 KDa cut-off membrane (Millipore Corporation, Bedford, Mass., USA) were followed to concentrate to 1/10 volume. This last process was repeated 3 times; each time with 10-x volume against distilled water. Then the content (5 ml) was subjected to gel filtration chromatography using Sephadex G-50 Fine (φ3×52 cm) column followed by lyophilization. Yield after lyophilization was 140 mg: ~ about 70%; by weight based on SMA and pirarubicin, 80% based on weight of pirarubicin.

Example 2

Determination of the Physicochemical and Biochemical Characteristics of the Invention (1) Gel Chromatography Gel filtration chromatography using Sephadex G-50 Fine (Pharmacia LKB, Uppsala, Sweden) was carried out to demonstrate the change in molecular weight after complexing reaction with SMA. The column size used was φ3×52 cm, with 0.25 M sodium hydrogen bicarbonate buffer (pH 8.24) as mobile phase. Each fraction volume was 6.5 ml. As shown in FIG. 1, the molecular size of the SMA-complex showed much larger size compared to both free pirarubicin and free SMA.

(2) Fluorescence Spectrum

Figure 2:
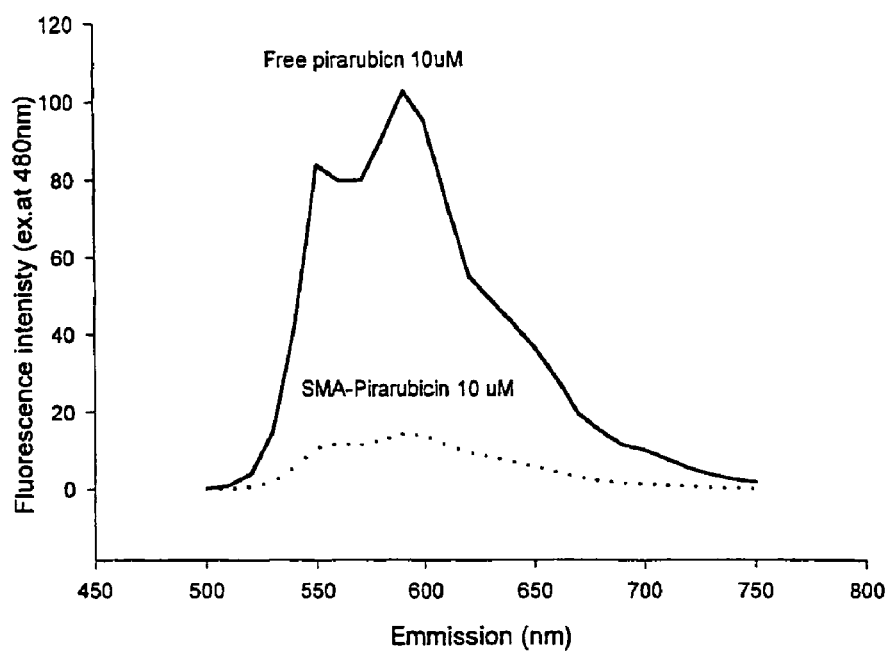
FIG. 2 shows the change of fluorescence intensity at the same molar concentration of the SMA-pirarubicin complex against free pirarubicin alone.

Free or unbound anthracyclin compounds show intense florescence emission spectrum peaked at both 550 nm and 590 nm when excited at 480 nm. This fluorescence is greatly quenched when the molecules is in close interacting vicinity with large polymer such as in micelles, or lipid capsules in the case of liposome due to energy transfer to aromatic residues in the micelle, liposome or lipidic milieu, resulting in efficient quenching or suppressed fluorescence. As shown in FIG. 2 the fluorescence spectrum of SMA pirarubicin complex was greatly quenched when compared with free form. Therefore, quenched fluorescence spectrum (intensity) could be used to prove encasement of pirarubicin in the micelle, or very close contact with aromatic residue of SMA.

Figure 3:
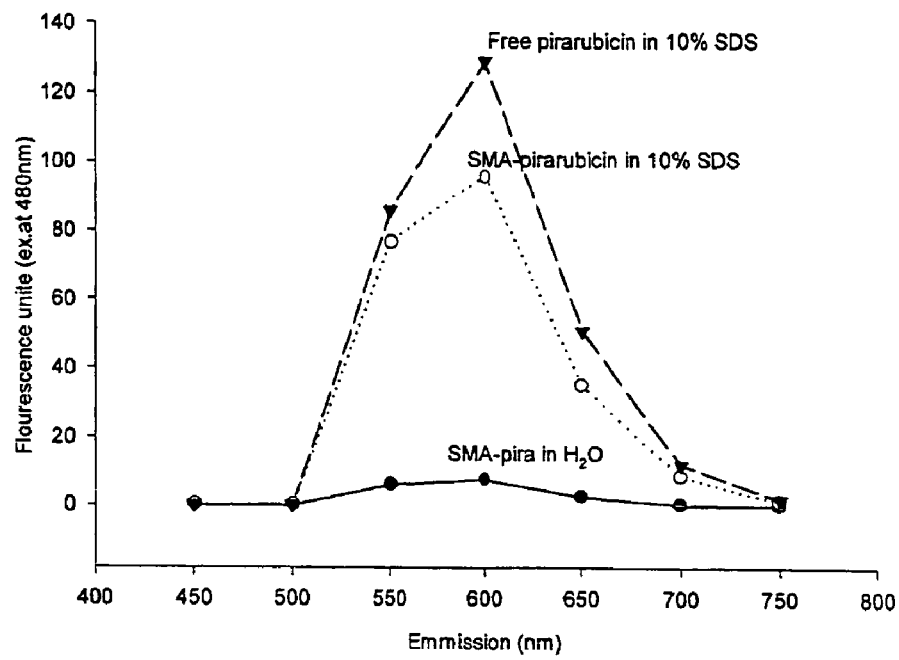
FIG. 3 shows the increase of fluorescence intensity of the SMA-pirarubicin complex in H$_2$O and in 10% SDS (Sodium dodecyl sulphate).
Figure 4:
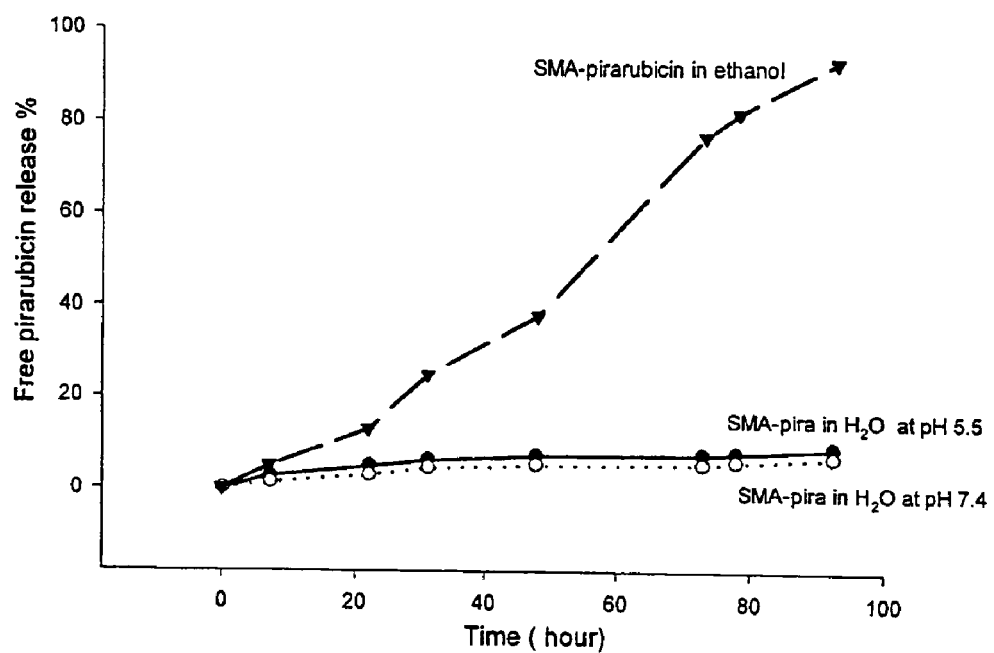
FIG. 4 shows time dependent release of pirarubicin from SMA-pirarubicin complex in vitro in aqueous media at different pHs and in ethanol.

Fluorescence intensity quenched by binding with SMA was regenerated when the micelle were exposed to 10% sodium dodecyl sulphate (SDS) as shown in FIG. 4. This phenomena supports formation of SMA micelle complex through non-covalent bond. Because SDS would disrupt the hydrophobic association of the micelle between the anthracyclin and the hydrophobic styrene residue of SMA. Namely, the fluorescence intensity of SMA-pirarubicin or SMA-doxorubicin conjugates/complexes became comparable to that of free pirarubicin or free doxorubicin upon disrupting of micelles by exposing in SDS solution as shown in FIG. 3.

Similarly, exposing of the micelles to, ethanol, which breaks non-covalent bonding of SMA-drug micelles, made fluorescence as intense as free drugs, similar to exposure to SDS solution.

(3) Release of Free Drug from the Dialysis Bag: Proof of Apparent Macromolecular Nature of SMA-Drug Complex It is of importance that large molecular weight polymeric drugs having apparent molecular size larger than 10.000, preferably more than 50 KDa such as SMA-anthracyclin micelles, to exert tumor seeking EPR-effect, and thereby ultimately releasing free drug. To verify the drug complexes of the present invention release free drug from the micelle or polymeric conjugate in vitro, 20 mg of SMA-doxorubicin conjugates or SMA-pirarubicin conjugates was dissolved in 5 ml $H_2O$ and placed in sealed dialysis bag (M. W cut off 1.000; Spectrapor, Spectrum Laboratories Inc. CA. USA.). The dialysis bag was submerged in 25 ml of $H_2O$ with adjusted pH either at 7.4 to resemble circulating blood or pH 5.5 for tumor tissue, using 0.01 M NaOH and 0.01 M HCl, and incubated at 37° C. for several days in the dark. In this setting free drug, either doxorubicin or pirarubicin per se, extravasated out of the dialysis tube within a few hours. The released pirarubicin or doxorubicin outside the dialysis bag was collected at predetermined time and amount was quantified by absorbance at 480 nm. The results are shown in FIG. 4.

As shown in FIG. 4, the release rate under such condition was very slow; about 3% per day with relatively higher release at lower pH for both compounds indicating that the stability of the conjugate micelle in circulation. When the outside solution was replaced by ethanol the release rate has increased tremendously indicating the disruption of the hydrophobic interaction in the complex between the anthracyclins and the styrene hydrophobic moiety of SMA. One can envisage this hydrophobic environment would be more close to the endosome after internalization of the polymeric micelle into cytoplasm of cancer cell by endocytosis. Therefore, the high rate of drug release would be brought about by the acidic more lipophilic milieu of malignant tissues after endocytotic internalization.

(4) Elemental Analysis

Elemental analyses of SMA-pirarubicin complex after purification (fractional precipitation, ultra filtration and column chromatography) for H, C, N and O in the micelle proved the composition percentage of the 2 major constituents of the micelle (SMA and either doxorubicin or pirarubicin). The results are in agreement with spectrophotometer data measuring the absorbance at 480 nm.

Example 3

In Vitro Cytotoxicity

In vitro cytotoxicity of SMA-(doxorubicin or pirarubicin) micelle complex was determined by the method using 3-(4, 5-dimethylthiazol-2-yl)-2,5-diphenyltetrazolium bromide (MTT assay) with both human colon cancer SW480 cells and human cervical cancer HeLa cells. They were plated in 96-well culture plates (Falcon, Becton Dickinson Labware, N.J., USA) at a cell density of 3000 cells/well. Cells were cultured overnight in Dulbecco's modified Eagle's medium with 10% fetal calf serum under 95% air and 5% $CO_2$. SW480 and HeLa cells were then incubated in the presence of native doxorubicin, pirarubicin or its SMA-complexes for 72 hours. Cytotoxicity was then quantified as the fraction of surviving cells relative to drug untreated controls (FIG. 5).

Figure 5:
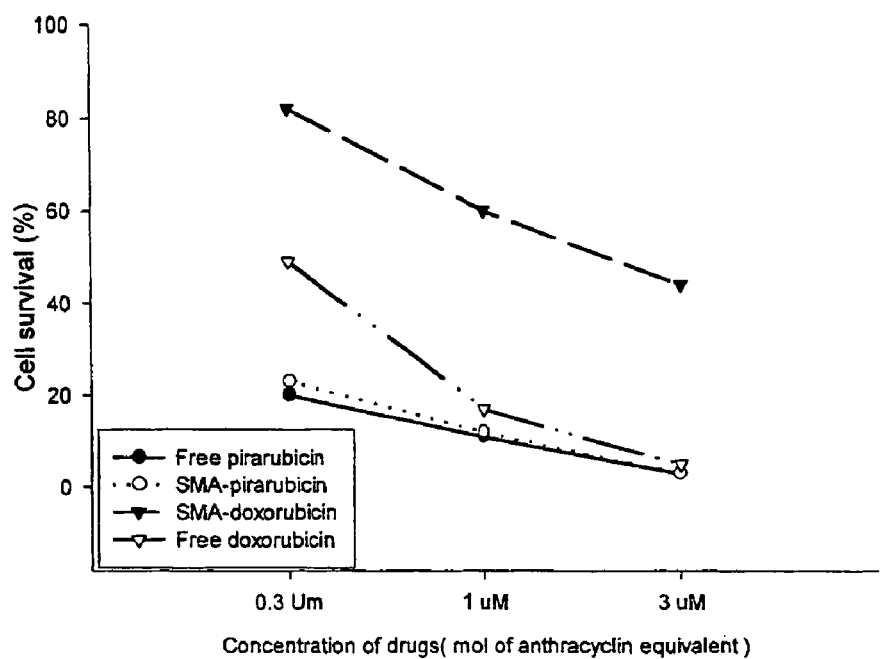
FIG. 5 shows in vitro cytotoxic effect of free pirarubicin and doxorubicin and their SMA micelle complexes against SW 480 human colon cancer cell line after 3 days of culture.
Figure 6:
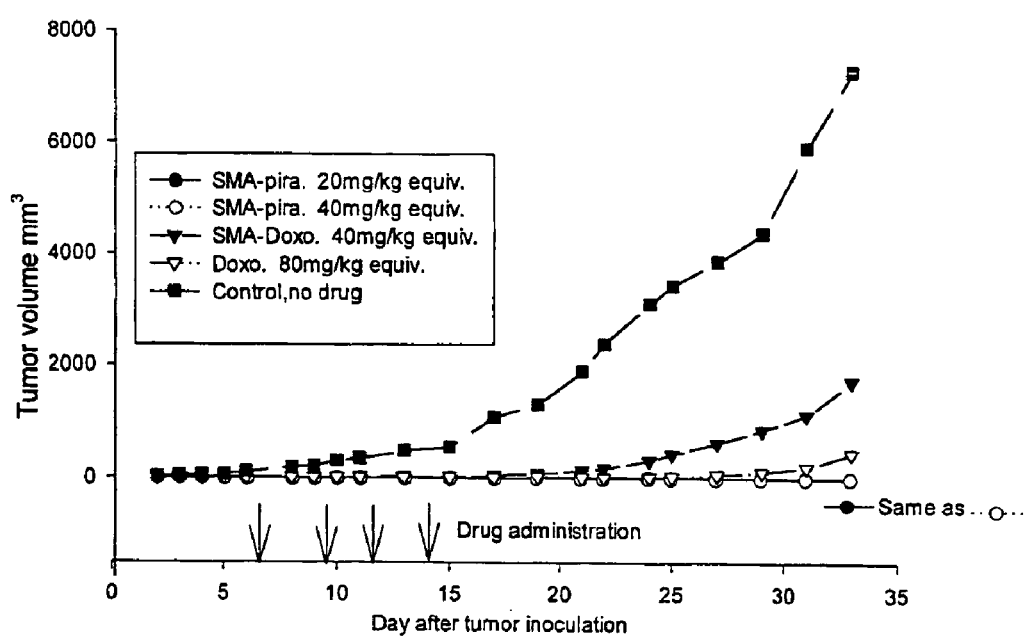
FIG. 6 shows the in vivo antitumor effect of SMA-pirarubicin and SMA-doxorubicin in ddY mice bearing S-180 mouse sarcoma at variable doses.

As shown in FIG. 5, SMA-pirarubicin exhibited almost similar cytotoxic effect in vitro to these cell lines when compared to free pirarubicin i.e. 85-100%). Cytotoxic activity of the SMA-doxorubicin micelle were considerably lower than that of the free doxorubicin (about 40%) which can be attributed to the higher hydrophobic property of doxorubicin having slower release rate, thus delaying the release of free drug available to cells in the culture medium. In conclusion SMA-anthracyclins polymer complexes have potential activity comparable to free parent drugs, or in case of doxorubicin, the activity was lower than free drug as seen in Doxorubicin.

Example 4

In Vivo Antitumor Activities

Figure 7:
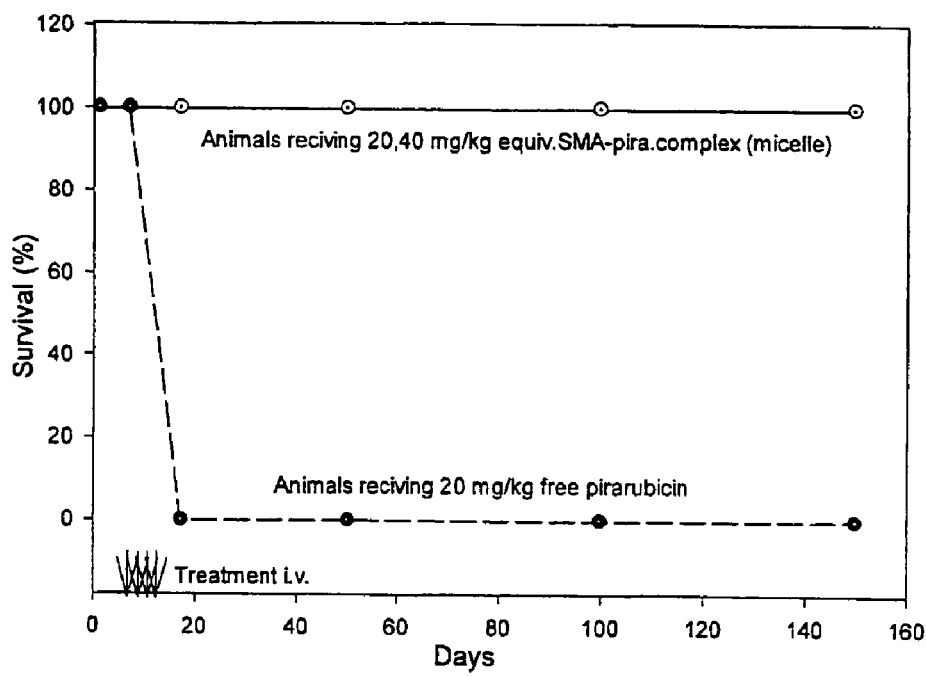
FIG. 7 shows the survival of animals treated with SMA-pirarubicin complex and free pirarubicin.

Male ddY mice of 6 weeks old were used. Sarcoma S180 cells ($2 \times 10^6$ cells per mouse) were implanted s.c. in the dorsal skin. At 7-10 days after tumor inoculation when tumors reached to a diameter of 5-7 mm, but no necrotic areas were apparent, the treatment by desired concentration of doxorubicin, pirarubicin or their SMA complexes were started. Drugs were dissolved in distilled water and administered iv to the mice tail vein according to predetermined schedules (See FIG. 7). The growth of the tumors was monitored every 2 days by measuring the tumor volume. As shown in FIG. 7, tumor growth suppression of SMA-pirarubicin complex was more active than SMA-doxorubicin complex.

Survival rate of mice receiving SMA-pirarubicin and free pirarubicin is shown in FIG. 7.

It is noteworthy that mice received dose of 20 or 40 mg/kg body weight of free pirarubicin equivalent of SMA complex for 4 consecutive days, all tumors were completely regressed. Obviously all treated animal survived 100% for more than 6 months. All animals receiving 20 mg/kg body weight of free pirarubicin or doxorubicin, as equivalent dose used for the complex, died within 1 week due to toxicity (FIG. 7). The complete eradication of tumor in all animals obtained with this invention is unprecedented with previously tested most, if not all, other antitumor agents.

Example 5

Synergic Tumor Model in Mice

Figure 8:
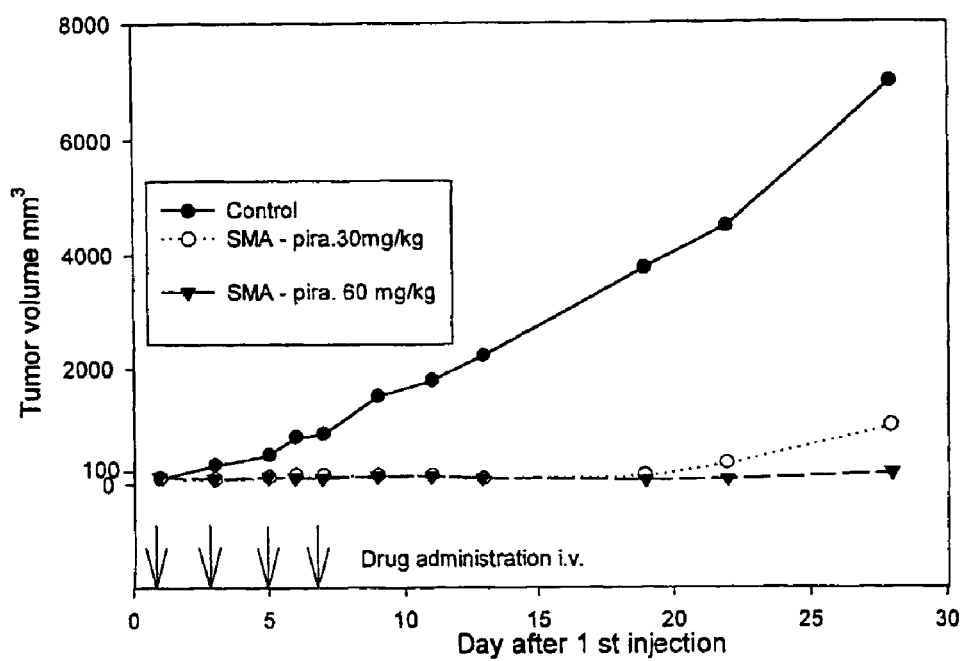
FIG. 8 shows growth suppression effect of SMA-pirarubicin in ddY mice bearing S-180 mouse sarcoma.

Similar to the above Example 4, another experiment using immunologically syngeneic mouse/tumor model was conducted. Tumor used was colon 38 adenocarcinoma originated from colon cancer. Tumor tissue of colon 38 tumor cells in block of about 30 mg/site was implanted bilaterally in dorsal skin of C57 BL mice. After 14 days when solid tumor is palpable size of ~100 mm in diameter, drug treatments were initiated using 50 mg/kg pirarubicin equivalent complex in a single dose administered i.v. Results showed that 100% of animals attained total recovery after 2 weeks of treatment, further demonstrating the promising potentiality of those agents. Results are shown in FIG. 8.

Example 6

Potential Side Effect of SMA-Pirarubicin and SMA-Doxorubicin Micelle Complexes S-180 bearing mice with tumors of about 5-7 mm in diameter were used for this study. Full blood analysis was performed weekly for 4 weeks before and after 1, 2 and 3 weeks of iv injections of either doxorubicin, pirarubicin or their SMA micelle complexes as described above. Blood biochemistry including, alanine aminotransferase (ALT), aspartate aminotransferase (AST), lactic dehydrogenase (LDH) and total creatine phosphokinase (CPK) were measured at 36 hr after i.v. administration of either free drugs or SMA-micelle complexes.

At the same time, the heart, spleen, liver and kidney tissues were stained with hematoxylin-eosin (H&E staining) for determination of cytological tissue toxicity. The micellar drugs showed no toxicity up to 100 mg/kg body weight when administered on 4 time injections (25 mg/kg×4) over one week, or 70 mg/kg when administered as a single dose. Blood count, cardiac and liver functions in animal receiving the complexes micellar drugs showed no significant difference from any drugs treated control animals.

Table 1 shows an example of complete blood count of animals for 3 weeks after drug administration, iv receiving 10 mg/kg of free pirarubicin versus animals receiving 20 mg/kg SMA-pirarubicin complex (20 mg/kg free pirarubicin equivalent), compared to no drug control in mice Remarkable safety of the drugs of the present invention should be noted which makes it highly promising for clinical trails.

TABLE 1

Hematologican toxicity of free pirarubicin and SMA-pirarubicin complex

|  | Control | Free pirarubicin 10 mg/kg | | | SMA-pirarubicin complex Equivalent as pirarubicin 20 mg/kg | | |
| --- | --- | --- | --- | --- | --- | --- | --- |
|  |  | 1 week | 2 week | 3 week | 1 week | 2 week | 3 week |
| Leucocyte (/mm³) | 8012 ± 565 | 2533 ± 108 | 5000 | 4500 | 6016.7 ± 576.8 | 5900 ± 754.7 | 6366.6 ± 675 |

TABLE 1-continued

Hematologican toxicity of free pirarubicin and SMA-pirarubicin complex

|  | Control | Free pirarubicin 10 mg/kg | | | SMA-pirarubicin complex Equivalent as pirarubicin 20 mg/kg | | |
| --- | --- | --- | --- | --- | --- | --- | --- |
|  |  | 1 week | 2 week | 3 week | 1 week | 2 week | 3 week |
| Hemoglobin (g/dL) | 14.9 ± 0.46 | 11.1 ± 0.9 | 12.1 | 15.7 | 15 ± 0.9 | 14.1 ± 0.56 | 15.9 ± 0.12 |
| Erythrocyte (×10,000/mm³) | 898 ± 35 | 490.6 ± 144 | 876 | 916 | 973 ± 57.8 | 861 ± 27.4 | 837.5 ± 39.3 |
| Thrombocyte (×1,000/mm³) | 132.9 ± 5.4 | 67.7 ± 0.9 | 130 | 143 | 141.3 ± 5.6 | 130.3 ± 3.8 | 120 ± 11.5 |
| Survival Rate (%) | 100 | 100 | 25 | 25 | 100 | 100 | 100 |

±: Standard Deviation

Example 7

Change in Molecular Weight of Cis-platinum

SMA-cis-platinum complex was prepared with SMA and cis-platinum in the same way as example 1, and the change of its molecular weight was determined (1) Gel Chromatography Sephadex G-50 Fine (Pharmacia LKB, Uppsala, Sweden) was used for gel chromatography under the following condition Mobile phase; 0.25M sodium bicarbonate buffer solution (pH8.24)

Column size; 45×1.5 cm

Volume of each fraction; 4 ml

Molecular weight before and after SMA-cis-platinum complex formation was determined.

Figure 9:
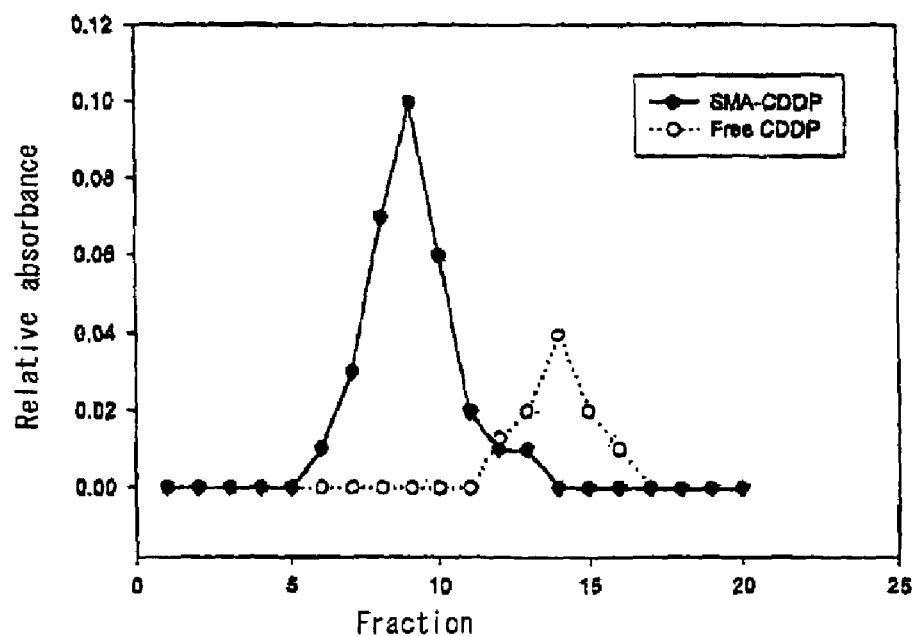
FIG. 9 is gel chromatogram indicating the increase of molecular weight of cis-platinum after formation of micelle FIG. 10 indicates cytotoxicity of SMA-cis-platinum micelle complex to human mammary tumor cell after three days of cell culture, in comparison with that of free cis-platinum

The result is shown in FIG. 9, which indicates increase in molecular weight through SMA-micelle complex formation.

(2) Determination of Membrane Permeability Through Molecular Sieve Membrane

The permeability of SMA cis-platinum complex and free cis-platinum was determined with molecule sieve membrane of maximum 3 KDa The result is shown in Table 2

TABLE 2

Concentration of free cis-platinum after ultra filtration through membrane of maximum 3 KDa

|  | Free Cis-platinum | SMA cis-platinum complex |
| --- | --- | --- |
| Permeated % through 3 Kda membrane | 100 | 1.4 |
| Not permeated % through 3 Kda membrane | 0 | 98.6 |

Concentration of free cis-platinum was determined with o-phenylenediamine colorimetric method at 720 nm Example 8

Cytotoxicity of SMA Cis-Platinum Micelle Complex and Free Cis-Platinum

Human mammary cancer cell was incubated in SMA-cis-platinum micelle complex (25 and 50 µg/ml) solution in a test tube for 72 hours in the same way as example 3.

Figure 10:
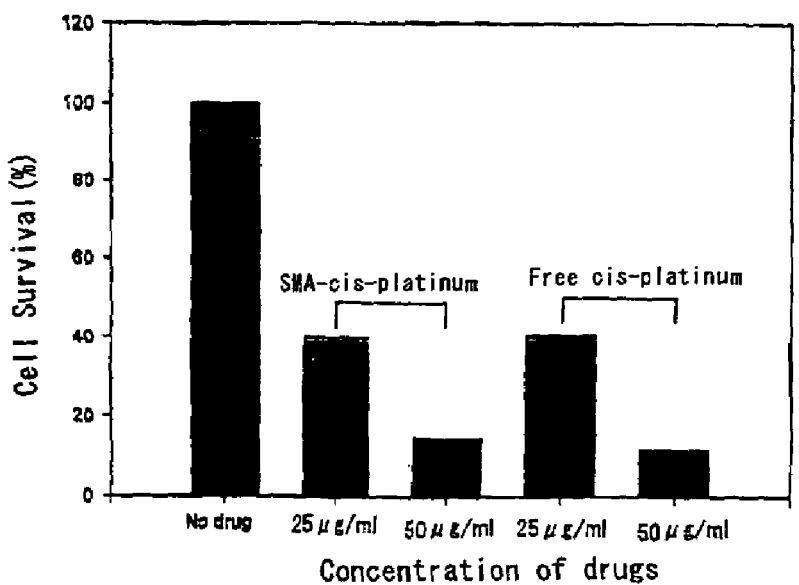

The cytotoxicity was expressed as ratio of survived cell together with those of no drug and free cis-platinum in FIG. 10. SMA cis-platinum micelle complex indicated its cytotoxicity against the above described tumor cell at the same extent as free cis-platinum.

Example 9

SMA-taxol Micelle Complex (1) SMA-Taxol Micelle Formation

Evidence of SMA-taxol micelle formation was examined by reacting following mixtures under the same condition as in SMA-pirarubicine micelle formation.

(a) SMA+Taxol alone (b) SMA+Taxol+EDAC

This procedure (a) showed no micelle formation even after 24 hrs, i.e. (Opaque/turbid) indicating insoluble state. In procedure (b) it became clear in 6-12 hrs micelle formation is suggested.

The preparation made in the procedure (b), did not pass through the ultra filtration membrane (UF-10, cut off 10 kDa).

(2) Gel Chromatography

Gel filtration chromatography using Sephadex G-50 was carried out to demonstrate the change in molecular weight after complexing reaction with SMA, in the same way as the Example 2.

Figure 11:
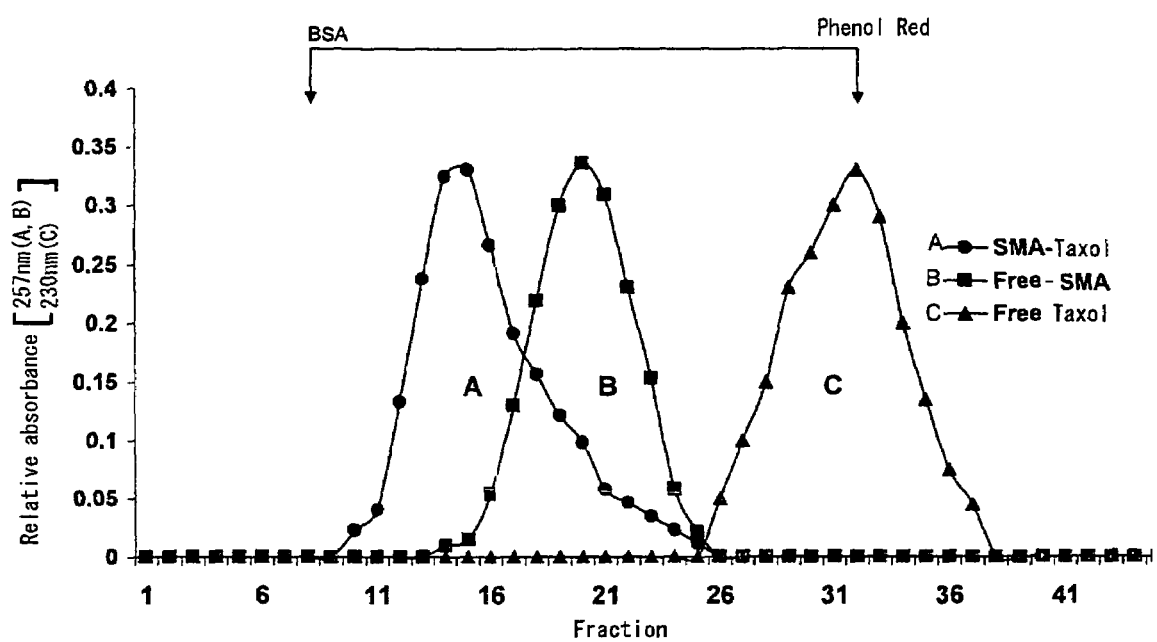
FIG. 11 is gel chromatogram indicating the increase of molecular weight of taxol after it formed micelle complex with SMA. In the figure, "A" is SMA-taxol micelle complex, "B" is free taxol; "C" is free SMA.
Figure 12:
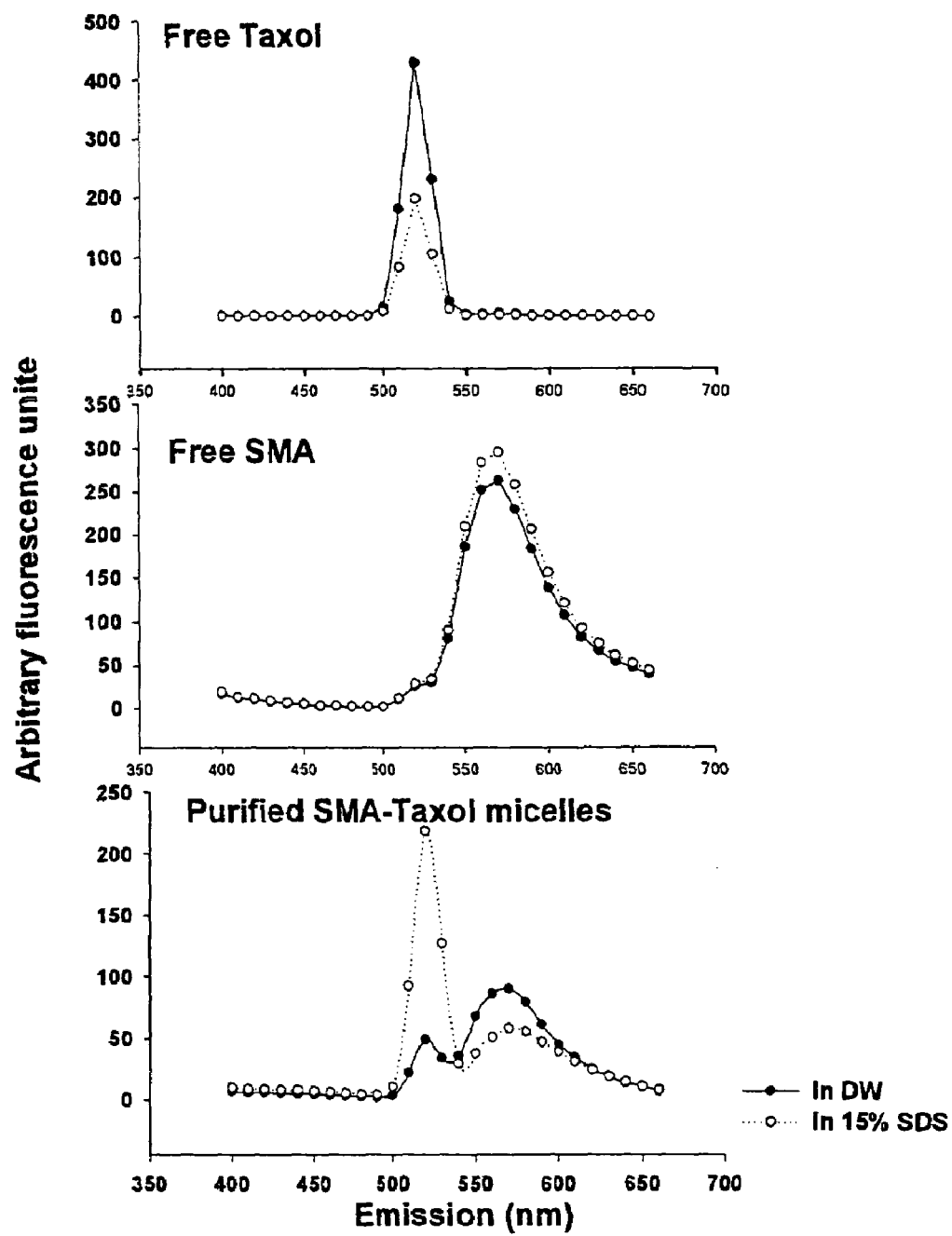
FIG. 12 indicates change in fluorescent intensity of free taxol, free SMA and SMA-taxol micelle complex in aqueous solution and 10% DSS solution.

Gel filtration condition is same as Example 2, except that, the column size used was 52×1.5 cm, with 0.2 M sodium hydrogen bicarbonate buffer (pH 8.1) as mobile phase. The SMA-taxol micelle eluted at void volume indicating the size larger than 10 kDa. The result is shown in FIG. 11. Standard molecular weight substance in the top of FIG. 11 is BSA (Bovine serum albumin) (67.5 Kda) and phenol red (354 Kda) This was further validated by G-150 column chromatography (3) Fluorescent Spectrum Fluorescent spectrum analysis was submitted to SMA-taxol micelle complex in the same way as Example 2-(2). As shown in FIG. 12(*a*), free taxol has peak at 525 nm in the fluorescent spectrum, but SMA-taxol; micelle complex lacks the peak in FIG. 12(*c*). However when the micelle was transferred into 15% dodecyl sodium sulfate, the spectrum appeared again (FIG. 12(*c*) dotted line) This indicates that bonding between SMA and taxol is non-covalent but forms micelle complex. The fluorescent intensity of SMA itself in SDS solution is almost same as that in aqueous solution. This suggests that SDS changed SMA-taxol bonding

INDUSTRIAL APPLICABILITY

The antitumor agent according to the present invention, taking advantage of EPR effect, may improve cancer treatment effect and reduce side effects to the normal organs and tissues to a large extent, by forming high molecular weight micelle complex of SMA and low molecular weight antitumor agent which itself has strong antitumor effect but little selective targeting to tumor cells.

In the present invention, stable micelle complex may be formed from SMA, antitumor agent and polyamines. The complex behaves as if 10 kDa or greater molecular weight polymer in human body. Further when it bind albumin through non-covalent bonding, it indicates apparent increase in molecular weight, so that it may be concentrated in tumor cells. As a result the present invention enables ten times as strong antitumor effect as low molecular weight antitumor agent against various cancer with minimum side effect, so that it is promising therapeutic drug for solid cancer.

The invention claimed is:

1. A polymeric antitumor agent comprising a polymeric micelle complex of an antitumor agent with styrene maleic acid copolymer (SMA), wherein the antitumor agent is bonded to the SMA through a non-covalent bond, wherein the antitumor agent is entrapped in the micelle, and wherein the antitumor agent is an anthracyclin antitumor agent.

2. A polymeric antitumor agent comprising a polymeric micelle complex of an antitumor agent with styrene maleic acid copolymer (SMA), wherein the antitumor agent is bonded to the SMA through a non-covalent bond, wherein the antitumor agent is entrapped in the micelle, and wherein the antitumor agent is cis-platinum.

3. A method of preparing the polymeric antitumor agent according to claim 1, comprising dissolving the styrene maleic acid copolymer and the antitumor agent in an aqueous solution, in the presence of water soluble carbodiimide, an amino acid or polyamine at a pH of 2 to 5, then increasing the pH to higher than 8, followed by neutralization, and finally recovering a polymer fraction by a polymer separation process.

4. A method of preparing the polymeric antitumor agent according to claim 2, comprising dissolving the styrene maleic acid copolymer and the antitumor agent in an aqueous solution, in the presence of water soluble carbodiimide, an amino acid or polyamine at a pH of 2 to 5, then increasing the pH to higher than 8, followed by neutralization, and finally recovering a polymer fraction by a polymer separation process.

* * * * *